(12) United States Patent
Turner et al.

(10) Patent No.: US 8,728,784 B2
(45) Date of Patent: May 20, 2014

(54) METHOD FOR FLUID FLOW CONTAINMENT IN AN OPEN LIQUID ENVIRONMENT

(75) Inventors: Kevin T. Turner, Madison, WI (US);
Kevin V. Christ, Madison, WI (US);
Justin Willians, Cambridge, WI (US);
Pedro J. Resto, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 900 days.

(21) Appl. No.: 12/774,417

(22) Filed: May 5, 2010

(65) Prior Publication Data

US 2011/0272035 A1 Nov. 10, 2011

(51) Int. Cl.
*B01L 3/00* (2006.01)

(52) U.S. Cl.
USPC ....... 435/173.6; 435/286.5; 436/63; 436/148; 422/82.13; 422/112; 422/504

(58) Field of Classification Search
USPC .......... 435/173.6, 286.5, 286.6, 287.1, 305.1; 436/63, 148; 422/82.13, 112, 502, 503, 422/504
See application file for complete search history.

(56) References Cited

U.S. PATENT DOCUMENTS

| | | | | |
|---|---|---|---|---|
| 6,300,108 B1 * | 10/2001 | Rubinsky et al. | ........... | 435/173.6 |
| 6,458,325 B1 * | 10/2002 | Roscher et al. | .............. | 422/504 |
| 7,435,587 B2 * | 10/2008 | Diresta et al. | ............. | 435/305.1 |

OTHER PUBLICATIONS

"Recent advances in electric analysis of cells in microfluidic systems", Bao et al, Anal Bioanal Chem (2008) 391:933-942.
"Biology on a Chip: Microfabrication for Studying the Behavior of Cultured Cells", Li et al, Biomedical Engineering, 31 (5&6):423-488 (2003).
"Microfluidic Shear Devices for Quantitative Analysis of Cell Adhesion", Lu et al, Anal Chem, 2004, 76, 5257-5264.
"Microfabrication in Biology and Medicine", Voldman et al, Annu Rev. Biomed. Eng. 1999, 01:401-425.
"Engineered systems for the physical manipulation of single cells", Voldman, Biotechnology 2006, 17:532-537.
"Application of microfluidics in chemical biology", Weibel et al, Chemical Biology 2006, 10:584-591.
"Microfluidics technology for manipulation and analysis of biological cells", Yi et al, Analytica Chimica Acta 560 (2006) 1-23.
"A plate reader-compatible microchannel array for cell biology assays", Yu et al, Lab Chip, 2007, 7, 388-391.

* cited by examiner

*Primary Examiner* — Eric Keasel
(74) *Attorney, Agent, or Firm* — Boyle Fredrickson, S.C.

(57) ABSTRACT

A method is provided for fluid flow containment in an open liquid environment at least partially defined by a surface. The method includes the step of positioning a microfluidic device over the surface. The microfluidic device defines a chamber having a height. A flow of fluid is applied in the chamber. The pressure of the flow of fluid is monitored and the height of the chamber is determined from the measured pressure of the flow of fluid.

35 Claims, 4 Drawing Sheets

METHOD FOR FLUID FLOW CONTAINMENT IN AN OPEN LIQUID ENVIRONMENT

REFERENCE TO GOVERNMENT GRANT

This invention was made with United states government support under 0845294 awarded by the National Science Foundation. The United states government has certain rights in this invention.

FIELD OF THE INVENTION

This invention relates generally to microfluidic environments, and in particular, to a method for fluid flow containment in an open liquid environment.

BACKGROUND AND SUMMARY OF THE INVENTION

Microfluidic devices have shown tremendous promise for the manipulation, control, and measurement of environments and processes in cell biology studies. Miniaturization provides multiple benefits including, but not limited to, shorter reaction times, better control through laminar flow and parallel measurements. Despite the numerous advantages of microfluidics in cell biology research, the adoption and use of the technology outside the labs specializing in microfluidics has been limited. The primary reason for this limited adoption of microfluidics in cell biology research is a lack of compatibility between microfluidic devices and traditional cell culture approaches. More specifically, microfluidic devices are closed channels fabricated from plastic and/or glass and require that cells be cultured or inserted into these closed channels in order to use the device for cell biology studies. Maintaining appropriate gas exchange and nutrient delivery for cell culture in channels is difficult and questions remain about comparing data from cells cultured in channels and cells grown using traditional methods.

Therefore, it is a primary object and feature of the present invention to provide a method for fluid flow containment in an open liquid environment.

It is a further object and feature of the present invention to provide a method for fluid flow containment in an open liquid environment that allows for compatibility between a microfluidic device and traditional cell culture approaches.

It is a still further object and feature of the present invention to provide a method for fluid flow containment in an open liquid environment that is simple to perform.

It is a still further object and feature of the present invention to provide a method for fluid flow containment in an open liquid environment that allows for a user to create a desired microfluidic environment around a cell.

In accordance with the present invention, a method is provided for fluid flow containment in an open liquid environment at least partially defined by a surface. The method includes the step of positioning a microfluidic device over the surface. The microfluidic device defines a chamber having a height. A flow of fluid is applied in the chamber and the pressure of the flow of fluid is monitored. Thereafter, the height of the chamber is determined by monitoring the pressure of the flow of fluid.

The microfluidic device includes an input port and an output port. The input and output ports are in communication with the chamber. A second input port may also be provided in the microfluidic device. The second input port also communicates with the chamber. Fluid is flowed into the chamber through the second input port to direct the flow of fluid over a user-selected portion of the surface. The step of applying the flow of fluid in the chamber may include the additional step of flowing fluid into the chamber through the input port. The fluid exits the chamber through the output port.

It is contemplated to deposit a cell on the surface such that the flow of fluid in the chamber provides hydrodynamic loading on the cell. The hydrodynamic loading on the cell may be varied. The hydrodynamic loading on the cell may be varied by varying the flow rate of the flow of fluid or by varying the height of the chamber. In addition, the hydrodynamic loading on the cell may be monotonically increased the over time.

An electric field may be generated that intersects the chamber by providing first and second spaced electrodes in communication with the chamber. A cell may be deposited on the surface such that the electric field intersects the cell.

In accordance with a further aspect of the present invention, a method is provided for fluid flow containment in an open liquid environment at least partially defined by a surface. The method includes the step of positioning a microfluidic device over the surface. The microfluidic device defines a chamber having a height and includes input and output ports in communication with the chamber. Fluid is flowed into the chamber through the input port. The fluid flowing in the chamber has a pressure and exits the chamber through the output port. The height of the chamber is adjusted in response to the pressure of the fluid flowing in the chamber.

Input port may be a first input port and the method may include the additional step of providing a second input port in the microfluidic device. The second input port also communicates with the chamber. Fluid flowing into the chamber through the second input port directs the flow of fluid over a user-selected portion of the surface.

It is contemplated to deposit a cell on the surface such that the fluid flowing in the chamber provides hydrodynamic loading on the cell. The hydrodynamic loading on the cell may be varied. The hydrodynamic loading on the cell may be varied by varying the flow rate of the flow of fluid or by varying the height of the chamber. In addition, the hydrodynamic loading on the cell may be monotonically increased the over time.

An electric field may be generated that intersects the chamber by providing first and second spaced electrodes in communication with the chamber. A cell may be deposited on the surface such that the electric field intersects the cell.

In accordance with a still further aspect of the present invention, a method is provided for fluid flow containment in an open liquid environment at least partially defined by a surface. The method includes the step of providing a microfluidic device having a lower surface and first and second horizontally spaced sidewalls depending therefrom. The microfluidic device is positioned over the surface such that the lower surface, the first and second sidewalls and the surface defines a chamber. Fluid is flowed into the chamber. The sidewalls are vertically spaced from the surface and confine the flowing fluid in the chamber.

The method may include the additional steps of depositing a cell on the surface in the chamber such that the fluid flowing in the chamber provides hydrodynamic loading on the cell; varying the hydrodynamic loading on the cell; and monitoring the cell for delamination from the surface.

The microfluidic device includes an input port and an output port. The input and output ports are in communication with the chamber. A second input port may be provided in the microfluidic device. The second input port also communicates with the chamber. Fluid is flowed into the chamber through the second input port to direct the fluid flowing in the chamber over a user-selected portion of the surface. A second output port may also be provided in the microfluidic device. The second output port also communicates with the chamber. Fluid flowing out of the chamber may also flow through the second output port.

The step of flowing fluid into the chamber includes the step of flowing fluid into the chamber through the input port. The fluid exiting the chamber flows through the output port. It is contemplated to vary the hydrodynamic loading on the cell by varying the flow rate of the flow of fluid or by varying the height of the chamber. In addition, the hydrodynamic loading on the cell may be monotonically increased the over time.

An electric field may be generated that intersects the chamber by providing first and second spaced electrodes in communication with the chamber. A cell may be deposited on the surface such that the electric field intersects the cell.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
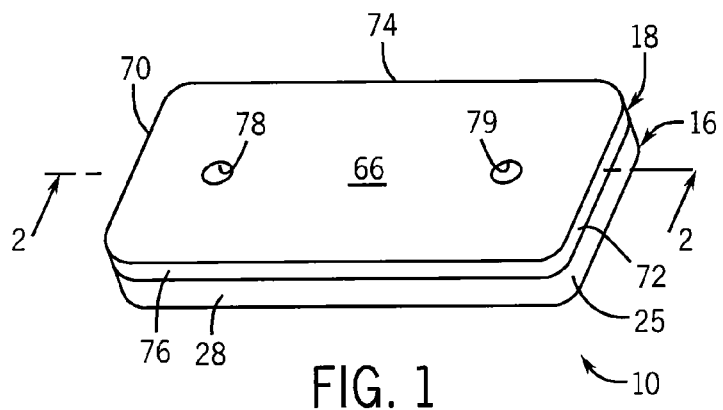
FIG. 1 is an isometric view of a microfluidic device for effectuating the methodology of the present invention.
Figure 2:
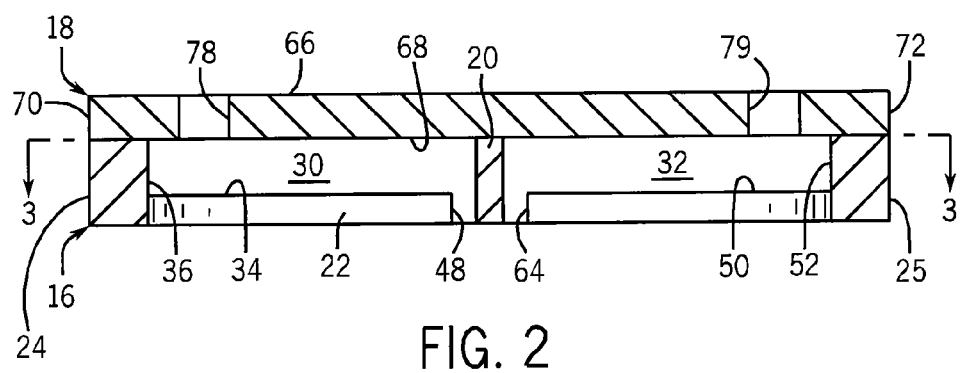
FIG. 2 is an enlarged, cross sectional view of the microfluidic device taken along line 2-2 of FIG. 1.
Figure 3:
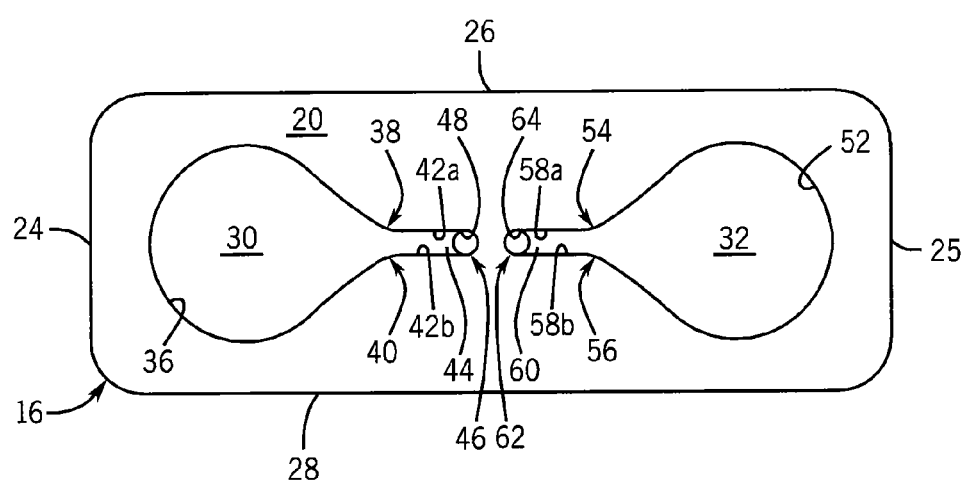
FIG. 3 is an enlarged, cross sectional view of the microfluidic device taken along line 3-3 of FIG. 2.

Referring to FIGS. 1-3 and 6, a microfluidic device for effectuating the methodology of the present invention is generally designated by the reference numeral 10. It is intended for device 10 to allow for fluid flow containment in an open liquid environment. The methodology of the present invention may be used in connection with a wide variety of applications including, but not limited to, the chemical treatment of cells, the patterning of proteins on a surface and/or the measuring of the adhesion strength of single cell 11 on surface 13 of traditional cell culture labware, e.g. a multiwell plate or Petri dish 15, as hereinafter described. Microfluidic device 10 is defined by first and second layers 16 and 18, respectively. First layer 16 is formed preferably from a silicon material and includes upper and lower surfaces 20 and 22, respectively, interconnected by first and second ends 24 and 25, respectively, and first and second sides 26 and 28, respectively. First and second spaced cavities 30 and 32, respectively, are formed in upper surface 20 of first layer 16.

First cavity 30 is defined by bottom surface 34 which is spaced from upper surface 20 of first layer 16 by generally arcuate sidewall 36. Sidewall 36 terminates at first and second opposite ends 38 and 40, respectively. First and second channel walls 42a and 42b, respectively, project from corresponding ends 38 and 40, respectively, of sidewall 36. First and second channel walls 42a and 42b, respectively, are generally parallel to each other and define first channel 44 therebetween. First channel 44 terminates at terminal end 46 which communicates with input opening 48. Input opening 48 extends between bottom surface 34 and lower surface 22 of first layer 16, for reasons hereinafter described.

Second cavity 32 is defined by bottom surface 50 spaced from upper surface 20 of first layer 16 by generally arcuate sidewall 52. Bottom surface 50 is generally co-planar with bottom surface 34. Sidewall 52 terminates at first and second opposite ends 54 and 56, respectively. First and second channel walls 58a and 58b, respectively, project from corresponding ends 54 and 56, respectively, of sidewall 52. First and second channel walls 58a and 58b, respectively, are generally parallel to each other and define second channel 60 therebetween. Second channel 60 is generally coaxial with first channel 44 and terminates at terminal end 62 which communicates with output opening 64. Output opening 64 extends between bottom surface 50 and lower surface 22 of first layer 16, for reasons herein after described.

Second layer 18 of microfluidic device 10 is formed preferably from a polymeric material and includes upper and lower surfaces 66 and 68, respectively, interconnected by first and second ends 70 and 72, respectively, and first and second sides 74 and 76, respectively. Lower surface 68 of second layer 18 is positioned on and bonded to upper surface 20 of first layer 16 such that first and second ends 70 and 72, respectively, of second layer 18 are generally coplanar with first and second ends 24 and 25, respectively, of first layer 16; and such that first and second sides 74 and 76, respectively, of second layer 18 are generally coplanar with first and second sides 26 and 28, respectively, of first layer 16. Second layer 18 further includes input 78 extending between upper and lower surfaces 66 and 68, respectively, that communicates with first cavity 30. In addition, second layer 18 includes output 79 extending between upper and lower surfaces 66 and 68, respectively, that communicates with second cavity 32.

Figure 4:
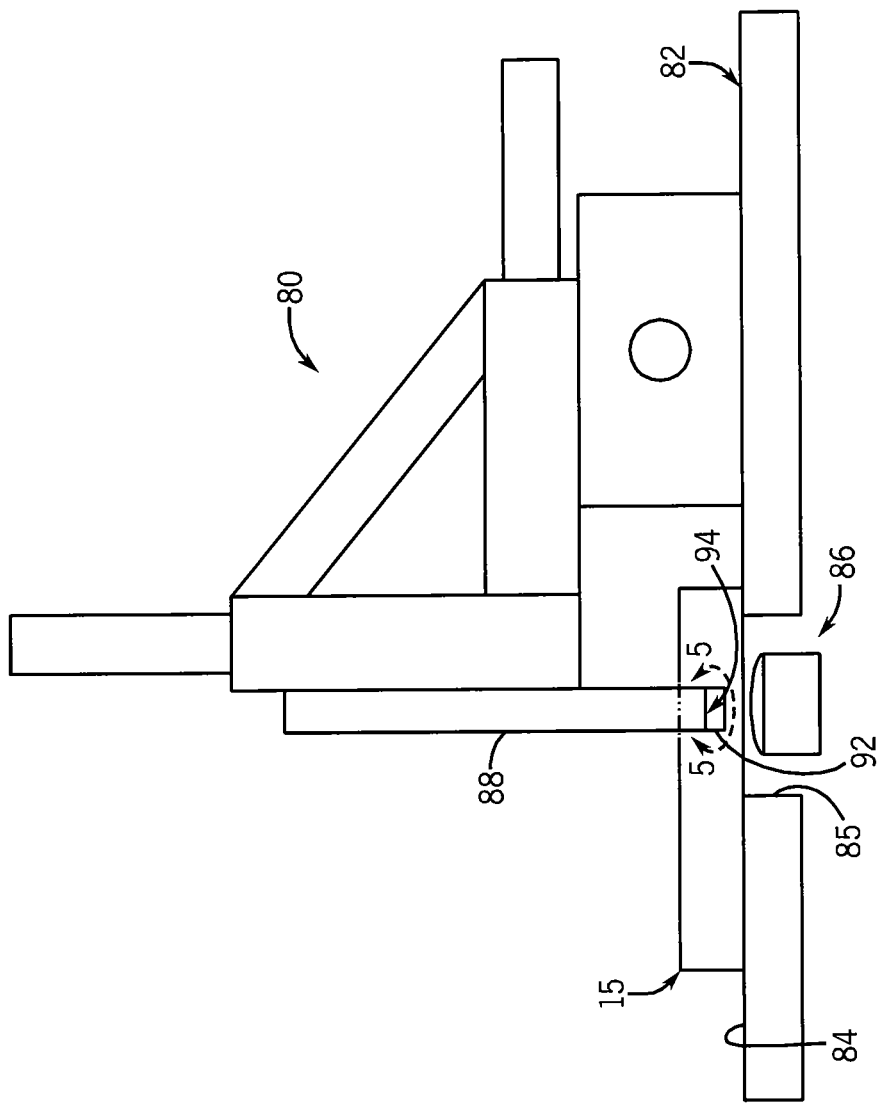
FIG. 4 is a schematic, side elevational view of a three axis stage for effectuating the methodology of the present invention.

Referring to FIG. 4, in order to properly position microfluidic device 10 with respect to surface 11 of Petri dish 15, three axis stage 80 is provided. As is conventional, stage 80 includes X-axis, Y-axis and Z-axis stages for moving microfluidic device 10 independently and precisely in the direction of the X-axis, the Y-axis or the Z-axis of rectangular coordinates. Three axis stage 80 further includes bottom plate 82 having an upper surface 84 adapted for receiving Petri dish 15 thereon. Bottom plate 82 is supported on a supporting surface (not shown) and includes an opening 85 therethrough to accommodate objective 86 of an inverted microscope (not shown). Support 88 is operatively connected to bottom plate 82 and extends vertically over opening 85. Lower end 90 includes device clamp 92 for releasably supporting microfluidic device 10 at a user selected position over surface 13 of Petri dish 15, FIG. 5, as hereinafter described. It is contemplated for bottom plate 82 to be the stage of the inverted microscope (not shown) and for bottom plate 82 to be angularly alignable such that surface 13 of Petri dish 15 is generally parallel to first layer 16 of microfluidic device 10.

Figure 5:
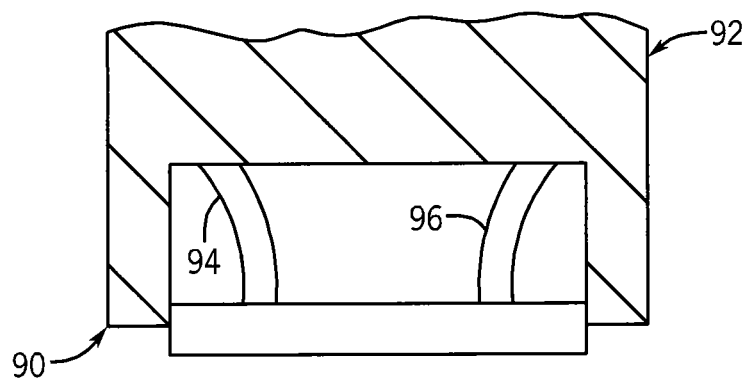
FIG. 5 is an enlarged, side elevational view of a clamping device of the three axis stage supporting the microfluidic device taken along line 5-5 of FIG. 4.
Figure 6:
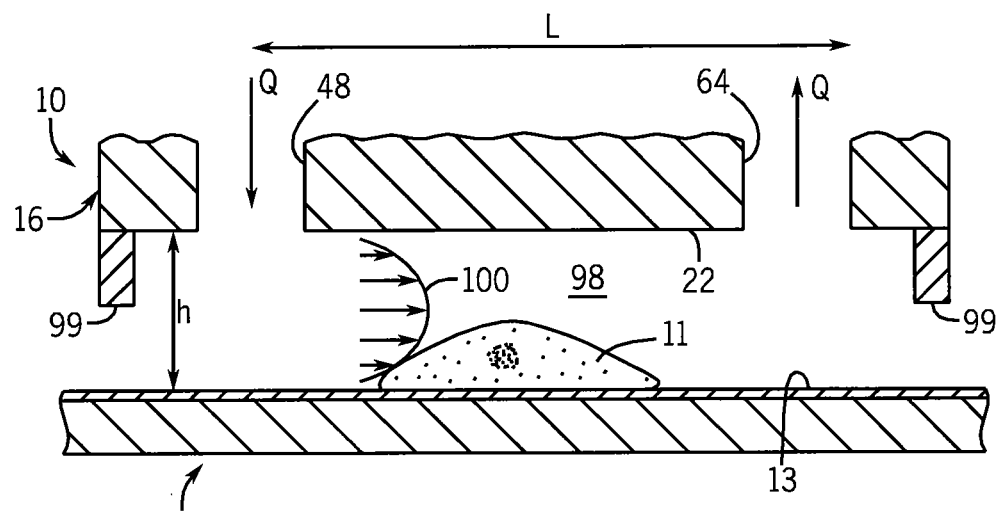
FIG. 6 is a cross sectional view of the microfluidic device of FIG. 1 positioned above a Petri dish to effectuate the methodology of the present invention.

In operation, microfluidic device 10 is mounted within device clamp 92 of three axis stage 80, FIG. 5. Input 78 and output 80 of second layer 18 of microfluidic device 10 are operatively connected to corresponding input and output tubes 94 and 96, respectively, which, in turn, are connected to syringe pumps (not shown) or the like in conventional manners. Referring to FIGS. 4 and 6, using three axis stage 80, microfluidic device 10 is positioned above single cell 11 within the cell culture fluid on surface 13 of Petri dish 15 such that a local microfluidic chamber 98 having a user selected height h is created between lower surface 22 of first layer 16 and surface 13 of Petri dish 15. By way of example, it is contemplated for the height h of microfluidic chamber 98 to be in the range of approximately 20 and 50 microns and the lateral distance L between input opening 48 and output opening 64 in first layer 16 of microfluidic device 10 to be approximately 400 to 1000 microns.

By maintaining the height h of microfluidic chamber 98 relatively small with respect to the lateral distance L between input opening 48 and output opening 64 in first layer 16 of microfluidic device 10, a flow field, generally designated by the reference numeral 100, is created between lower surface 22 of first layer 16 and surface 13 of Petri dish 15. By injecting fluid into flow field 100 through input opening 48 using the syringe pump, laminar flow of the fluid from input opening 48 to output opening 64 is achieved. It is noted that microfluidic device 10 is not physically connected to Petri dish 15, and hence, can be moved in x, y and z directions using three axis stage 80. As such, microfluidic device 10 can be placed at any location adjacent upper surface 13 of Petri dish 15 and used to create local microfluidic flow. Short walls 99 depend from lower surface 22 of first layer 16 to assist in confinement of the microfluidic flow in microfluidic chamber 98.

In the case wherein the height h of microfluidic chamber 98 is smaller (at least 3-4× times smaller) than the lateral distance L between input opening 48 and output opening 64, the flow-rate Q through input and output openings 48 and 64, respectively, and the difference in fluidic pressure ΔP between the outlet and inlet openings 48 and 64, respectively, are related by the following expression:

$$\Delta P = C\left(\frac{\mu L}{wh^3}\right)Q \quad \text{Equation (1)}$$

wherein: ΔP is the pressure difference between inlet and outlet openings 48 and 64, respectively; C is a constant dependant on the geometry of inlet and outlet openings 48 and 64, respectively; L is the effective length between inlet and outlet openings 48 and 64, respectively; w is the effective width of microfluidic chamber 98; h is the height of microfluidic chamber 98; and Q is the flow rate of the fluid through input and output openings 48 and 64, respectively.

It can be appreciated that constant C; the effective length L between input and output openings 48 and 64, respectively; and the effective width w of microfluidic chamber 98 are fixed for a given microfluidic device 10. Further, the flow rate of the fluid through input and output openings 48 and 64, respectively, may be set by the syringe pumps. Hence, the pressure difference ΔP between the input and output openings 48 and 64, respectively, is only a function of the height of microfluidic chamber 98. As a result, it can be appreciated that by measuring the pressure difference ΔP between the input and output openings 48 and 64, respectively, the height h of microfluidic chamber 98 may be determined, thus allowing for closed loop control of the operation of microfluidic device 10. In other words, a control system may be implemented to maintain the height h of microfluidic chamber 98 simply by monitoring the pressure difference ΔP between the input and output openings 48 and 64, respectively.

As heretofore described, the methodology of the present invention may be used in connection with a wide variety of applications including, but not limited to, the chemical treatment of cells, the patterning of proteins on a surface and/or the measuring of the adhesion strength of single cell 11 on surface 13 of traditional cell culture labware, e.g. a multiwall plate or Petri dish 15. By way of example, in order to measure adhesion strength of cell 11 on a protein coated surface 13 of Petri dish 15, fluid is injected into input 78 of second layer 18 of microfluidic device 10 by a first syringe pump (not shown) so as to introduce fluid into first cavity 30 and first channel 44. As the fluid flows into microfluidic chamber 98 through input opening 48, the syringe pump operatively connected to tube 96 acts to aspirate cell culture fluid though output opening 64. As described, fluid injected into microfluidic chamber 98 will flow over cell 11 and generates a shear stress on cell 11 that is linearly proportional to the flow rate of the fluid flowing through microfluidic chamber 98 and fluid viscosity, and inversely proportional to the square of the height h of microfluidic chamber 98. Thus, the hydrodynamic loading on cell 11 can be controlled by changing the flow rate (e.g., through a computer-controlled syringe pump) or by changing the height h of microfluidic chamber 98. (e.g., by adjusting the position of microfluidic device 10 with respect to single cell 11 within the cell culture fluid on surface 13 of Petri dish 15 utilizing three axis stage 80). In a typical cell adhesion test, the shear stress on cell 11 would be monotonically increased with time, as heretofore described, and cell 11 would be monitored utilizing objective 86 of an inverted microscope (not shown). At a critical shear stress, cell 11 delaminates from surface 13 of Petri dish 15 and the stress applied to cell 11 at delamination is defined as a shear strength.

As described, the methodology of the present invention allows for the local application of fluid flow to a cell, thereby permitting single-cell mechanics measurements. Further, the small dimensions of microfluidic chamber 98 allow for high shear stresses to be applied on cell 11 while the fluid flowing in microfluidic chamber 98 is maintained in the laminar regime. This arrangement differs from larger conventional assays wherein the switch from laminar flow to turbulent flow often limits the maximum shear stress that can be applied to a cell. As noted, the methodology of the present invention can be applied to cells cultured on a broad range of surfaces, including cells in Petri dishes, as heretofore described. In addition, the methodology of the present invention is compatible with existing microscopy techniques commonly used in the life sciences. Again, as previously noted, while the methodology of the present invention is described for use in connection with measuring the adhesion strength of single cell 11 on surface 13 of traditional cell culture labware, the methodology of the present invention may be used in connection with other applications including, but not limited to, the chemical treatment of cells, the patterning of proteins on a surface and/or the applying local hydrodynamic loads to cells in order to study their response to mechanical stimuli, without deviating from the scope of the present invention.

Figure 7:
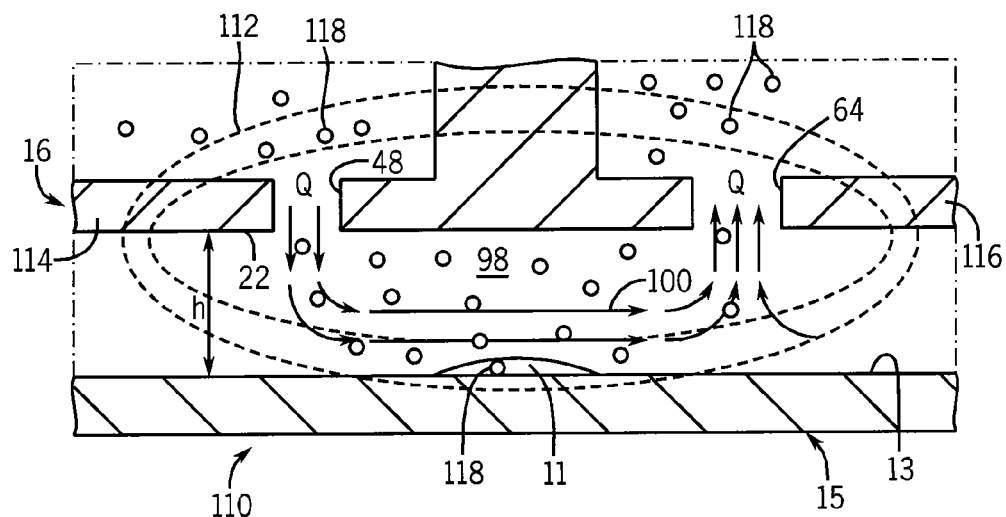
FIG. 7 is a cross sectional view of an alternate embodiment of a microfluidic device positioned above a Petri dish to effectuate the methodology of the present invention

Referring to FIG. 7, an alternate embodiment of a microfluidic device for effectuating the methodology of the present invention is generally designated by the reference numeral 110. It can be appreciated that microfluidic device 110 is identical to microfluidic device 10, except as hereinafter provided. As such, the previous description of microfluidic device 10 is understood to describe the common elements of microfluidic device 110, as if fully described herein. Common reference characters are used in order to facilitate understanding.

In order to selectively treat a single cell in the open environment defined by microfluidic device 110, the concepts of electroporation and hydrodynamically confined fluid flow are contemplated. As is known, electroporation is the application of an electrical field to a cell, e.g. cell 11, in order to induce a change in the cell's membrane which facilitates the transport of large molecules that normally could not cross into the cell. Electroporation is often used to improve transfection efficiency. As heretofore described, the methodology of the present invention allows for the precise geometry of flow field 100 to be controlled such that flow field 100 may be directed over a single, desired cell 11 that may, in turn, be surrounded by many other cells. In this fashion, cell 11 in a Petri dish 15 can be treated.

In order to generate electric field 112, first and second spaced electrodes 114 and 116, respectively, are mounted to lower surface 22 of first layer 16 at locations adjacent input and output openings 48 and 64, respectively. First and second electrodes 114 and 116, respectively, are electrically coupled to a power source (not shown) in a conventional matter. In response to the charging of first and second electrodes 114 and 116, respectively, electric field 112 is generated.

In operation, with electric field 112 generated, it is contemplated to inject fluid having cell treatments 118 contained therein into input 78 of second layer 18 of microfluidic device 110 with a first syringe pump (not shown) so as to introduce fluid into first cavity 30 and first channel 44. As the fluid flows into microfluidic chamber 98 through input opening 48, the syringe pump operatively connected to tube 96 acts to aspirate cell culture fluid though output opening 64. As described, fluid injected into microfluidic chamber 98 will flow over cell 11. As heretofore described, electroporation of cell 11 with electric field 112 induces a change in the membrane of cell 11 which facilitates the transport of large molecules into cell 11.

Various modes of carrying out the invention are contemplated as being within the scope of the following claims particularly pointing out and distinctly claiming the subject matter which is regarded as the invention.

We claim:

1. A method for fluid flow containment in an open liquid environment at least partially defined by a surface, comprising the steps of:
   positioning a microfluidic device having an input port, an output port, and an exterior over the surface, the exterior of the microfluidic device and the surface defining a chamber therebetween having a height;
   applying a flow of fluid in the chamber from the input port to the output port along a path;
   monitoring the pressure of the flow of fluid;
   determining the height of the chamber in response to the pressure of the flow of fluid in the chamber; and
   maintaining the height of the chamber within a range to contain the flow of fluid within the chamber along the path;
   wherein:
   the chamber partially defines the open liquid environment such that the chamber communicates with an environment external of the microfluidic device.

2. The method of claim 1 wherein the input and output ports are in communication with the chamber.

3. The method of claim 2 further comprising the additional steps of:
   providing a second input port in the microfluidic device, the second input port communicating with the chamber; and
   flowing fluid into the chamber through the second input port to direct the flow of fluid over a user-selected portion of the surface.

4. The method of claim 2 wherein the step of applying the flow of fluid in the chamber includes the step of flowing fluid into the chamber through the input port, the fluid exiting the chamber through the output port.

5. The method of claim 1 comprising the additional step of:
   depositing a cell on the surface such that the flow of fluid in the chamber provides hydrodynamic loading on the cell; and
   varying the hydrodynamic loading on the cell.

6. The method or claim 5 wherein the flow of fluid has a flow rate and wherein the step of varying the hydrodynamic loading on the cell includes the additional step of varying the flow rate of the flow of fluid.

7. The method of claim 5 wherein the step of varying the hydrodynamic loading on the cell includes the additional step of monotonically increasing the hydrodynamic loading on the cell over time.

8. The method of claim 5 wherein the step of varying the hydrodynamic loading on the cell includes the additional step of varying the height of the chamber.

9. The method of claim 8 wherein the height of the chamber is less than 100 microns.

10. The method of claim 1 comprising the additional step of generating an electric field that intersects the chamber.

11. The method of claim 10 wherein the step of generating an electric field includes the step of providing first and second spaced electrodes in communication with the chamber.

12. The method of claim 10 comprising the additional step of depositing a cell on the surface such that the electric field intersects the cell.

13. A method for fluid flow containment in an open liquid environment at least partially defined by a surface, comprising the steps of:
   positioning a microfluidic device over the surface, the microfluidic device:
   defining a chamber having a height, the chamber partially defining the open liquid environment; and
   including input and output ports in communication with the chamber;
   flowing fluid into the chamber through the input port, the fluid flowing along a path in the chamber, having a pressure and exiting the chamber through the output port;
   adjusting the height of the chamber to a range in response to the pressure of the fluid flowing in the chamber to contain the flow of fluid within the chamber along the path.

14. The method of claim 13 wherein the input port is a first input port and wherein the method comprises the additional steps of:
   providing a second input port in the microfluidic device, the second input port communicating with the chamber; and
   flowing fluid into the chamber through the second input port to direct the flow of fluid over a user-selected portion of the surface.

15. The method of claim 13 comprising the additional step of:
   depositing a cell on the surface such that the fluid flowing in the chamber provides hydrodynamic loading on the cell; and
   varying the hydrodynamic loading on the cell.

16. The method of claim 15 wherein the fluid flowing in the chamber has a flow rate and wherein the step of varying the hydrodynamic loading on the cell includes the additional step of varying the flow rate of the flow of fluid.

17. The method of claim 15 wherein the step of varying the hydrodynamic loading on the cell includes the additional step of monotonically increasing the hydrodynamic loading on the cell over time.

18. The method of claim 15 wherein the step of varying the hydrodynamic loading on the cell includes the additional step of varying the height of the chamber.

19. The method of claim 18 wherein the range of the height of the chamber is less than 100 microns.

20. The method of claim 13 comprising the additional step of generating an electric field that intersects the chamber.

21. The method of claim 20 wherein the step of generating an electric field includes the step of providing first and second spaced electrodes in communication with the chamber.

22. The method of claim 20 comprising the additional step of depositing a cell on the surface such that the electric field intersects the cell.

23. A method for fluid flow containment in an open liquid environment at least partially defined by a containment surface, comprising the steps of:
   providing a microfluidic device having a lower surface and first and second horizontally spaced sidewalls depending therefrom;
   positioning the microfluidic device over the containment surface at a height such that the lower surface, the first and second sidewalls and the surface defining a chamber providing at least a portion of the open liquid environment;
   flowing fluid into the chamber, the fluid flowing along a path in the chamber and having a pressure; and
   adjusting the height of the chamber in response to the pressure of the fluid flowing in the chamber to contain the flow of fluid within the chamber along the path;
wherein the sidewalls are vertically spaced from the containment surface.

24. The method of claim 23 further comprising the steps of:
   depositing a cell on the containment surface in the chamber such that the fluid flowing in the chamber provides hydrodynamic loading on the cell;
   varying the hydrodynamic loading on the cell; and
   monitoring the cell for delamination from the surface.

25. The method of claim 24 wherein the fluid flowing in the chamber has a flow rate and wherein the step of varying the hydrodynamic loading on the cell includes the additional step of varying the flow rate of the fluid flowing.

26. The method of claim 24 wherein the step of varying the hydrodynamic loading on the cell includes the additional step of monotonically increasing the hydrodynamic loading on the cell over time.

27. The method of claim 24 wherein the step of varying the hydrodynamic loading on the cell includes the additional step of varying the height of the chamber.

28. The method of claim 27 wherein the height of the chamber is less than 100 microns.

29. The method of claim 23 wherein the microfluidic device includes an input port and an output port, the input and output ports in communication with the chamber.

30. The method of claim 29 further comprising the additional steps of:
   providing a second input port in the microfluidic device, the second input port communicating with the chamber; and
   flowing fluid into the chamber through the second input port to direct the fluid flowing in the chamber over a user-selected portion of the surface.

31. The method of claim 29 further comprising the additional steps on
   providing a second output port in the microfluidic device, the second output port communicating with the chamber; and
   flowing fluid out of the chamber through the second output port.

32. The method of claim 29 wherein the step of flowing fluid into the chamber includes the step of flowing fluid into the chamber through the input port, the fluid exiting the chamber through the output port.

33. The method of claim 23 comprising the additional step of generating an electric field that intersects the chamber.

34. The method of claim 33 wherein the step of generating an electric field includes the step of providing first and second spaced electrodes in communication with the chamber.

35. The method of claim 33 comprising the additional step of depositing a cell on the containment surface such that the electric field intersects the cell.

* * * * *